(12) United States Patent
Roby et al.

(10) Patent No.: US 9,146,233 B2
(45) Date of Patent: Sep. 29, 2015

(54) DETECTING MOLECULAR INTERACTIONS BY FLUORESCENCE RESONANCE ENERGY TRANSFER ON A SOLID-PHASE SUPPORT

(75) Inventors: Philippe Roby, Montreal (CA); Stephane Parent, Montreal (CA)

(73) Assignee: PerkinElmer Health Sciences, Inc., Waltham, MA (US)

( * ) Notice: Subject to any disclaimer, the term of this patent is extended or adjusted under 35 U.S.C. 154(b) by 503 days.

(21) Appl. No.: 11/939,471

(22) Filed: Nov. 13, 2007

(65) Prior Publication Data

US 2008/0261239 A1  Oct. 23, 2008

Related U.S. Application Data

(60) Provisional application No. 60/865,522, filed on Nov. 13, 2006.

(51) Int. Cl.
  *G01N 33/542* (2006.01)
  *G01N 33/533* (2006.01)
  *G01N 33/543* (2006.01)
  *G01N 33/58* (2006.01)

(52) U.S. Cl.
  CPC ............ *G01N 33/542* (2013.01); *G01N 33/533* (2013.01); *G01N 33/54313* (2013.01); *G01N 33/582* (2013.01); *G01N 33/585* (2013.01); *G01N 2440/14* (2013.01); *G01N 2458/40* (2013.01); *Y10T 436/143333* (2015.01)

(58) Field of Classification Search
  None
  See application file for complete search history.

(56) References Cited

U.S. PATENT DOCUMENTS

| | | | |
|---|---|---|---|
| 4,499,052 A | 2/1985 | Fulwyler | |
| 4,642,334 A | 2/1987 | Moore et al. | |
| 5,028,545 A | 7/1991 | Soini | |
| 5,622,821 A * | 4/1997 | Selvin et al. ............... | 435/6 |
| 5,709,994 A | 1/1998 | Pease et al. | |
| 5,981,180 A | 11/1999 | Chandler et al. | |

(Continued)

FOREIGN PATENT DOCUMENTS

| | | |
|---|---|---|
| EP | 0 345 776 | 11/1994 |
| WO | WO 99/30160 | 6/1999 |

(Continued)

OTHER PUBLICATIONS

Wang et al. AlphaScreen™: A Highly Sensitive, Nonradioactive and Homogeneous Assay Platform for Drug Discovery High Throughput Screening, Genomics, and Life Science Research Applications in Miniaturized Format (2002); Chapter 3 in: Microfabricated Sensors; Kordal, R. et al.; ACS Symposium Series, American Chemical Society, Washington, DC, pp. 45-56.*

(Continued)

*Primary Examiner* — Christine Foster
(74) *Attorney, Agent, or Firm* — Fish & Richardson P.C.

(57) ABSTRACT

The present disclosure features a variety of compositions, kits, and methods that are useful for, inter alia, detecting and/or analyzing an interaction between two molecules, a target molecule and a target-specific binding agent which can be, e.g., proteins, nucleic acids, saccharides or polysaccharides, small molecules, or combinations of any of the foregoing. The compositions, kits, and methods can also be used, e.g., to detect the presence or absence of an enzymatic activity (e.g., a kinase activity, a protease activity, or a phosphatase activity) in a sample; to identify a compound that modulates an interaction between two molecules; or to identify compounds that modulate the activity of an enzyme.

14 Claims, 3 Drawing Sheets

◆ Desferal-Fe3+
⊙ Phosphate group
▬ Dye (e.g. Alexa 647)

(56) References Cited

U.S. PATENT DOCUMENTS

| | | | |
|---|---|---|---|
| 5,998,146 A * | 12/1999 | Latva et al. | 435/6.11 |
| 6,251,581 B1 | 6/2001 | Ullman et al. | |
| 6,703,248 B1 * | 3/2004 | Singh et al. | 436/518 |
| 2002/0081617 A1 | 6/2002 | Buranda et al. | |
| 2002/0081688 A1 * | 6/2002 | Kamb et al. | 435/189 |
| 2002/0197606 A1 * | 12/2002 | Craig | 435/6 |
| 2004/0075907 A1 | 4/2004 | Moon et al. | |
| 2004/0125424 A1 | 7/2004 | Moon et al. | |
| 2004/0126875 A1 | 7/2004 | Putnam et al. | |
| 2004/0130761 A1 | 7/2004 | Moon et al. | |
| 2004/0130786 A1 | 7/2004 | Putnam et al. | |
| 2004/0132205 A1 | 7/2004 | Moon et al. | |
| 2004/0179267 A1 | 9/2004 | Moon et al. | |
| 2004/0249586 A1 | 12/2004 | Boge et al. | |
| 2005/0287548 A1 | 12/2005 | Bao et al. | |
| 2006/0009381 A1 | 1/2006 | Reutelingsperger et al. | |
| 2006/0019279 A1 | 1/2006 | Bosse et al. | |
| 2006/0063219 A1 | 3/2006 | Kuo et al. | |
| 2006/0115864 A1 | 6/2006 | Issakani et al. | |
| 2006/0121544 A1 | 6/2006 | Boge et al. | |
| 2006/0148104 A1 | 7/2006 | Marini et al. | |
| 2006/0166376 A1 * | 7/2006 | Craig et al. | 436/525 |
| 2006/0223158 A1 | 10/2006 | Liu et al. | |
| 2007/0087452 A1 | 4/2007 | Parker et al. | |
| 2010/0304404 A1 | 12/2010 | Boge et al. | |

FOREIGN PATENT DOCUMENTS

| | | | |
|---|---|---|---|
| WO | WO 99/42838 | 8/1999 | |
| WO | WO 01/84157 | 11/2001 | |
| WO | WO 03/008927 A2 * | 1/2003 | |
| WO | WO 2004/086049 A1 * | 10/2004 | G01N 33/58 |
| WO | WO 2006/078618 | 7/2006 | |

OTHER PUBLICATIONS

Kokko et al. "Europium(III) chelate-dyed nanoparticles as donors in a homogeneous proximity-based immunoassay for estradiol" Analytica Chimica Acta 503 (2004) 155-162.*

Niedlands, "Siderophores: Structure and Function of Microbial Iron Transport Compounds", the Journal of Biological Chemistry vol. 270 (1995), pp. 26723-26726.*

Banks and Paquette, "Comparison of three common amine reactive fluorescent probes used for conjugation to biomolecules by capillary zone electrophoresis," *Bioconjug. Chem.*, 1995, 6(4):447-458.

Bergendahl et al., "Luminescence Resonance Energy Transfer-Based High-Throughput Screening Assay for Inhibitors of Essential Protein-Protein Interactions in Bacterial RNA Polymerase," *Appl. Environ. Microbiol.*, 2003, 69(3):1492-1498.

Brinkley, "A brief survey of methods for preparing protein conjugates with dyes, haptens, and cross-linking reagents," *Bioconjug. Chem.*, 1992, 3:2-13.

Brody and Gold, "Aptamers as therapeutic and diagnostic agents," *Rev. Mol. Biotechnol.*, 2000, 74:5-13.

Burton and Harding, "Hydrophobic charge induction chromatography: salt independent protein adsorption and facile elution with aqueous buffers," *J. Chromatogr. A,* 1998, 814:71-81.

Cane et al., "Harnessing the biosynthetic code: combinations, permutations, and mutations," *Science*, 1998, 282:63-68.

Coligan et al. (eds.), "Fragmentation of Immunoglobulin G," *Current Protocols in Immunology*, 1991, Sections 2.8 and 2.10, Wiley Interscience.

Hartmann et al., "Selective DNA attachment of micro- and nanoscale particles to substrates," *J. Mater. Res.*, 2002, 17(2):473-478.

Haugland, "Coupling of monoclonal antibodies with fluorophores," *Meth. Mol. Biol.*, 1995, 45:205-221.

Hudson and Kortt, "High avidity scFv multimers; diabodies and triabodies," *J. Immunol Meth.*, 1999, 231:177-189.

Huston and George, "Engineered antibodies take center stage," *Hum. Antibodies*, 2001, 10:127-142.

Kanofsky, "Singlet oxygen production by chloroperoxidase-hydrogen peroxide-halide systems," *J. Biol. Chem.*, 1984, 259(9):5596-5600.

Kim et al., "Substrate specificities and identification of putative substrates of ATM kinase family members," *J. Biol. Chem.*, 1999, 274(53):37538-37543.

Klostermeier and Millar, "Time-resolved fluorescence resonance energy transfer: a versatile tool for the analysis of nucleic acids," *Biopolymers*, 2002, 61(3):159-179.

Meldal, "The One-Bead Two-Compound Assay for Solid Phase Screening of Combinatorial Libraries," *Biopolymers Peptide Science*, 2002, 66:93-100.

Myers, "Will combinatorial chemistry deliver real medicines?" *Curr. Opin. Biotechnol.*, 1997, 8:701-707.

Peloquin et al., "Conjugation of fluorophores to tubulin," *Nat. Meth.*, 2005, 2(4):299-303.

Poljak, "Production and structure of diabodies," *Structure*, 1994, 2(12):1121-1123.

Ribeiro et al., "The brain-derived neurotrophic factor rs6265 (Val66Met) polymorphism and depression in Mexican-Americans," *Neuroreport*, 2007, 18(12):1291-1293.

Song et al., "Synthesis and characterization of volatile metal β-diketonate chelates of $M(DPM)_n$ (M=Ce, Gd, Y, Zr, n=3,4) used as precursors for MOCVD," *J. Crystal Growth*, 2003, 250(3):423-430.

Stocks, "Intrabodies: production and promise," *Drug Discov. Today*, 2004, 9(22):960-966.

Voloshin et al., "Mono-thio-β-diketones—a new type of ligands suitable for sensitization of lanthanide luminescence. Infrared luminescence of an intensely colored neodymium and ytterbium mono-thio-β-diketonate chelates," *J. Luminescence*, 2001, 93(2):115-118.

Wheeler et al., "Intrabody and intrakine strategies for molecular therapy," *Mol. Ther.*, 2003, 8(3):355-366.

Yang et al., "Identification of -R-X-(X)-S/T-$X_3$-S/T- as Consensus Sequence Motif for Autophosphorylation-dependent Protein Kinase," *J. Biol. Chem.*, 1994, 269(47):29855-29859.

Zhang et al., "Nucleic acid aptamers in human viral disease," *Arch. Immunol. Ther. Exp.*, 2004, 52:307-315.

Supplementary European Search Report in EP Application 07 86 8748 mailed Nov. 3, 2009, 6 pages.

Australian Office Action; Application No. 2007323920; issued Aug. 23, 2012; 4 pages.

European Communication; Application No. 07868748.0-2404; mailed Oct. 1, 2012; 5 pages.

European Communication; Application No. 07868748.0-2404; mailed Dec. 5, 2011; 7 pages.

International Search Report and Written Opinion; Application No. PCT/US07/84576; mailed Oct. 22, 2008; 12 pages.

European Communication; Application No. 07868748.0-1408; mailed Oct. 10, 2013; 5 pages.

Canada Intellectual Property Office, Examiner's Report, CA Appl. No. 2,669,878, mailed on Feb. 6, 2014, 3 pages.

Canadian Intellectual Property Office, Examiner's Report, CA Appl. No. 2,669,398, mailed on Aug. 21, 2014, 2 pages.

\* cited by examiner

DETECTING MOLECULAR INTERACTIONS BY FLUORESCENCE RESONANCE ENERGY TRANSFER ON A SOLID-PHASE SUPPORT

CROSS-REFERENCE TO RELATED APPLICATIONS

This application claims priority under 35 U.S.C. §119 to U.S. Application Ser. No. 60/865,522, filed Nov. 13, 2006, the entire contents of which are hereby incorporated by reference.

SUMMARY

The disclosure relates to, inter alia, detecting and/or analyzing an interaction between two molecules (e.g., a target molecule and a target-selective binding agent). The compositions and methods featured herein are useful in a variety of applications including, but not limited to, detecting the presence or absence of an enzymatic activity (e.g., a kinase activity, a protease activity, or a phosphatase activity) in a sample or to screen for compounds that modulate (e.g., inhibit or enhance) an interaction between two molecules or the activity of an enzyme.

In one aspect, the disclosure features a composition comprising: a first solid-phase support associated with a target-selective binding agent and a first member of a fluorescence resonance energy transfer (FRET) pair; and a target molecule associated with (or comprising) a second member of the FRET pair, wherein the target molecule is not associated with a second solid-phase support. The first solid-phase support can be non-covalently or covalently bound to the target-selective binding agent. The first solid-phase support can be covalently or non-covalently bound to the first member of the FRET pair or the first solid-phase support can comprise (e.g., physically incorporated into, or adsorbed onto, the solid-phase support) for the first member of the FRET pair. The target-selective binding agent or target molecule can comprise deferoxamine and a trivalent metal cation (e.g., $Fe^{3+}$). The target-selective binding agent or the target molecule can comprise an antibody or target-selective binding fragment thereof. The antibody or antigen-binding fragment can be selected from the group consisting of a humanized antibody, a fully human antibody, a single chain antibody, a chimeric antibody, an $F_{ab}$ fragment, an $F_{(ab')2}$ fragment, an $F_{ab'}$ fragment, an $F_v$ fragment, and an $scF_v$ fragment. The first solid-phase support can be, e.g., an assay plate, a particle, or any other solid-phase support described herein.

In some embodiments, the target-selective binding agent or the target molecule can be, or contain, a polypeptide, a nucleic acid, a carbohydrate, a small molecule, or a combination of any of the foregoing.

In some embodiments, the target-selective binding agent can preferentially bind to a target molecule that comprises a modification as compared to a target molecule that does not comprise a modification. The target molecule can comprise a modification selected from the group consisting of a phosphomonoester moiety, a saccharide moiety, a ubiquitin moiety, an acetyl moiety, a SUMO moiety, a farnesyl moiety, and a geranyl-geranyl moiety.

In some embodiments, the target molecule can preferentially bind to a target-selective binding agent that comprises a modification as compared to a target-selective binding agent that does not comprise a modification. The target-selective binding agent can comprise a modification selected from the group consisting of a phosphomonoester moiety, a saccharide moiety, a ubiquitin moiety, an acetyl moiety, a SUMO moiety, a farnesyl moiety, and a geranyl-geranyl moiety.

In some embodiments, the first member of the FRET pair is a FRET donor and the second member of the FRET pair is a FRET acceptor. In some embodiments, the second member of the FRET pair is a FRET donor and the first member of the FRET pair is a FRET acceptor. In some embodiments, the first solid-phase support comprises a reagent capable of exciting the FRET donor. The reagent can excite the FRET donor by generating singlet oxygen. The reagent can be, e.g., phtalocyanine; methylene blue; rose bengal; a porphyrin; 9-alkylidene-N-alkyl acridans; enolethers; enamines; 9-alkylidene xanthenes; and endoperoxides such as such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide.

In some embodiments, one or both of the first member of the FRET pair and the second member of the FRET pair is fluorescent. The first member of the FRET pair and/or the second member of the FRET pair can be a fluorescent dye. The fluorescent dye can be, e.g., an ALEXA FLUOR® dye, an allophycocyanin (APC) dye, a carboxyfluorescein dye, a tetramethyl-6-carboxyrhodamine (TAMRA) dye, or any other fluorescent dye known to those of ordinary skill in the art or that are described herein.

In some embodiments, the first member of the FRET pair or the second member of the FRET pair can be a lanthanide chelate such as, e.g., DELFIA®, LANCE®, and TruPoint™ lanthanide chelates; "TEKES" (4-(4-isothio-cyanatophenylethynyl-2,6-{N,N-bis(carboxymethyl)aminomethyl]-pyridine)-based lanthanide chelates; ethylenediamine tetraacetic acid (EDTA)-based lanthanide chelates; DTPA-based lanthanide chelates; DOTA-based lanthanide chelates; DOPTA-based lanthanide chelates; europium cryptate; or any LanthaScreen™ lanthanide chelates. The lanthanide of the chelate can be, e.g., europium, terbium, samarium, or dysprosium.

In some embodiments, the composition can contain at least two first solid-phase supports, wherein each first solid-phase support is associated with a different target-selective binding agent.

In some embodiments, the composition can be in suspension or in solution. In some embodiments, the compositions can be frozen or lyophilized. In some embodiments, the composition can contain an aqueous buffer solution in which the composition forms a suspension or solution.

In some embodiments, the composition can comprise a first solid-phase support comprising a lanthanide chelate, wherein the first solid-phase support is a particle and wherein the first solid-phase support is bound to a target-selective binding agent; and a target molecule comprising a fluorescent dye, wherein the target molecule is not associated with a second solid-phase support.

In some embodiments, the composition can comprise: a first solid-phase support comprising two or more of: a lanthanide chelate, phthalocyanine, and thioxene, wherein the first solid-phase support is a particle and wherein the first solid-phase support is bound to a target-selective binding agent; and a target molecule comprising a fluorescent dye, wherein the target molecule is not associated with a second solid-phase support.

In another aspect, the disclosure features a composition comprising a mixture of first solid-phase supports, wherein the mixture comprises two or more pluralities of first solid-phase supports, wherein at least two of the two or more pluralities comprising first solid-phase supports are associated with different target-selective binding agents, and wherein the first solid-phase supports are also independently associated with a first member of a fluorescence resonance energy transfer (FRET) pair; and a target molecule associated with (or comprise) a second member of the FRET pair, wherein the target molecule is not associated with a second solid-phase support.

In another aspect, the disclosure features a method for detecting a target molecule (or a method for detecting the binding between a target-selective binding agent and a target molecule). The method includes the steps of: (optionally) providing: a first solid-phase support associated with a target-selective binding agent and a first member of a fluorescence resonance energy transfer (FRET) pair; and a target molecule associated with a second member of the FRET pair, wherein the target molecule is not associated with a second solid-phase support; contacting the target-selective binding agent with the target molecule (or contacting the first solid-phase support with the target molecule); and detecting binding of the target molecule to the target-selective binding agent. The method can also include the step of, after contacting the target-selective binding agent with the target molecule, separating the first solid-phase support from the unbound target molecule. The method can also include the step of covalently or non-covalently binding the target-selective binding agent to the first solid-phase support. The target molecule and target-selective binding agent can be, e.g., any of those described herein.

In yet another aspect, the disclosure features a method for identifying a compound that modulates the binding between a target molecule and a target-selective binding agent. The method includes the steps of: contacting, in the presence of a candidate compound, a first solid-phase support and a target molecule, wherein the first solid-phase support is associated with a target-selective binding agent and a first member of a fluorescence resonance energy transfer (FRET) pair and wherein the target molecule is associated with a second member of the FRET pair, and wherein the target molecule is not associated with a second solid-phase support; and detecting binding of the target molecule to the target-selective binding agent, wherein a difference in binding of the target molecule to the target-selective binding agent in the presence of the candidate compound as compared to the binding in the absence of the candidate compound indicates that the candidate compound modulates the interaction between the target-selective binding agent and the target molecule. The method can also include the step of, after contacting the first solid-phase support bound to a target-selective binding agent with the target molecule, separating the first solid-phase support from the unbound target molecule. The method can also include the step of covalently or non-covalently binding the target-selective binding agent to the first solid-phase support. The target molecule and target-selective binding agent can be, e.g., any of those described herein.

In some embodiments of the above methods, the first member of the FRET pair is a FRET donor and the second member of the FRET pair is a FRET acceptor. In some embodiments, the second member of the FRET pair is a FRET donor and the first member of the FRET pair is a FRET acceptor. In some embodiments, detecting can comprise measuring the amount of an emission produced from the FRET acceptor.

In some embodiments of the above methods, the candidate compound can inhibit or enhance the binding between the target-selective binding agent and the target molecule.

In some embodiments of the above methods, decreased binding between the target molecule and the target-selective binding agent in the presence of a candidate compound as compared to the amount of binding in the absence of the compound indicates that the compound inhibits the interaction between the target-selective binding agent and the target molecule.

In some embodiments of the above methods, increased binding between the target molecule and the target-selective binding agent in the presence of a candidate compound as compared to the amount of binding in the absence of the compound indicates that the compound enhances the interaction between the target-selective binding agent and the target molecule.

In some embodiments of the above methods, a first set of the first solid-phase support and target molecule and a second set of the first solid-phase support and target molecule are contacted with different candidate compounds at the same time.

In yet another aspect, the disclosure features a method for detecting an enzymatic activity in a sample, which method includes the steps of: contacting one or both of a first solid-phase support and a target molecule with a sample, wherein the first solid-phase support is associated with a target-selective binding agent and a first member of a fluorescence resonance energy transfer (FRET) pair and the target molecule is associated with a second member of the FRET pair and wherein the target molecule is not associated with a second solid-phase support; contacting the first solid-phase support with the target molecule; and detecting binding of the target molecule to the target-selective binding agent, wherein a difference in binding of the target-selective binding agent to the target-selective binding agent in the presence of the sample as compared to the binding in the absence of the sample indicates the presence or amount of an enzymatic activity in the sample.

In another aspect, the disclosure features a method for detecting an enzymatic activity in a sample. The method includes the steps of: contacting, in the presence of a sample, a first solid-phase support and a target molecule, wherein the first solid-phase support is associated with a target-selective binding agent and a first member of a fluorescence resonance energy transfer (FRET) pair and the target molecule is associated with a second member of the FRET pair and wherein the target molecule is not associated with a second solid-phase support; and detecting binding of the target molecule to the target-selective binding agent, wherein a difference in binding of the target molecule to the target-selective binding agent in the presence of the sample as compared to the binding in the absence of the sample indicates the presence or amount of an enzymatic activity in the sample. The sample can contain an enzymatic activity capable of modifying the target-selective binding agent or the target molecule. The enzymatic activity can be, e.g., a protease activity, a kinase activity, a phosphatase activity, a phosphodiesterase activity, a nucleotide cyclase activity, a ubiquitin ligase activity, a DNA polymerase activity, an RNA polymerase activity, a DNA ligase activity, or an isomerase activity.

In some embodiments of any of the methods above, decreased binding between the target molecule and the target-selective binding agent in the presence of a sample as compared to the amount of binding in the absence of the sample indicates the presence or amount of an enzymatic activity in the sample.

In some embodiments of any of the methods above, increased binding between the target molecule and target-selective binding agent in the presence of a sample as compared to the amount of binding in the absence of the sample indicates the presence or amount of an enzymatic activity in the sample.

In some embodiments of any of the above methods, a first set of the first solid-phase support and target molecule and a second set of the first solid-phase support and target molecule are contacted with different candidate compounds at the same time.

In some embodiments of any of the above methods, the first member of the FRET pair is a FRET donor and the second member of the FRET pair is a FRET acceptor. In some embodiments, the second member of the FRET pair is a FRET donor and the first member of the FRET pair is a FRET acceptor. In some embodiments, detecting can comprise measuring the amount of an emission produced from the FRET acceptor.

In yet another aspect, the disclosure features a method for identifying a compound that modulates the activity of an enzyme, which method includes the step of: providing: a first solid-phase support associated with a target-selective binding agent and a first member of a fluorescence resonance energy transfer (FRET) pair; a target molecule comprising a second member of the FRET pair, wherein the target molecule is not associated with a second solid-phase support; and an enzyme capable of modifying one or both of the target-selective binding agent and the target molecule; contacting, in the presence of the enzyme and a candidate compound, the first solid-phase support and the target molecule; and detecting binding of the target molecule to the target-selective binding agent, wherein a difference in binding of the target molecule to the target-selective binding agent in the presence of the candidate compound as compared to the binding in the absence of the candidate compound indicates that the candidate compound modulates the activity of the enzyme.

In another aspect, the disclosure features a method for identifying a compound that modulates the activity of an enzyme, which method includes the step of: providing: a first solid-phase support associated with a target-selective binding agent and a first member of a fluorescence resonance energy transfer (FRET) pair; a target molecule comprising a second member of the FRET pair, wherein the target molecule is not associated with a second solid-phase support; and an enzyme capable of modifying one or both of the target-selective binding agent and the target molecule; contacting one or both of the target-selective binding agent and the target molecule with the enzyme and a candidate compound; contacting the target-selective binding agent with the target molecule; and detecting binding of the target molecule to the target-selective binding agent, wherein a difference in binding of the target molecule to the target-selective binding agent in the presence of the candidate compound as compared to the binding in the absence of the candidate compound indicates that the candidate compound modulates the activity of the enzyme.

In some embodiments of any of the methods above, modification of one of both of the target molecule and the target-selective binding agent by the enzyme inhibits the interaction between the target molecule and the target-selective binding agent. In some embodiments of any of the methods above, modification of one of both of the target molecule and the target-selective biding agent by the enzyme enhances the interaction between the target molecule and the target-selective binding agent.

In some embodiments, the candidate compound can inhibit or enhance the activity of the enzyme.

In some embodiments of any of the above methods, the enzyme can be, e.g., a protease, a kinase, a phosphatase, a phosphodiesterase, a nucleotide cyclase, a ubiquitin ligase, a DNA polymerase, an RNA polymerase, a DNA ligase, or an isomerase.

In yet another aspect, the disclosure features a kit comprising: a first solid-phase support associated with a target-selective binding agent and a first member of a fluorescence resonance energy transfer (FRET) pair; a target molecule comprising a second member of the FRET pair, wherein the target molecule is not associated with a second solid-phase support; and instructions for detecting the binding of a target molecule to a target-selective binding agent. The kit can also include a control compound that inhibits or enhances the binding between the target molecule and the target-selective binding agent. The kit can also include an assay vessel such as a multi-well assay plate.

In some embodiments, the kit can also include one or more reagents for performing an enzymatic reaction such as, e.g., a kinase reaction, a phosphatase reaction, a phosphodiesterase reaction, or a protease reaction. The one or more reagents can be, e.g., a nucleotide triphosphate, a magnesium salt, and/or a manganese salt.

In some embodiments, the kit can also include a control sample. The control sample can contain at least one enzyme at a known concentration.

In some embodiments, the kit can also include a wash buffer and/or a solution that enhances FRET between the first and second member of the FRET pair.

In yet another aspect, the disclosure features a kit comprising one or more of any of the compositions described herein.

In another aspect, the disclosure features a kit comprising a first solid-phase support associated with a target-selective binding agent and a first member of a fluorescence resonance energy transfer (FRET) pair; a second member of the FRET pair; and instructions for covalently or non-covalently binding the second member of the FRET pair to a target molecule. The kit can also include a target molecule.

As used herein, "associated with" in the context of an interaction between two or more atoms or molecular units, includes any covalent or non-covalent bonding, or physical admixture, of two or more atoms or molecular units (e.g., a target molecule and a second member of a FRET pair or a target-selective binding agent and a molecule such as a linker bound to a first solid-phase particle). The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). It is understood that the term "associated with" (e.g., in the context of a first solid-phase support and a first member of a FRET pair and/or a target-selective binding agent) is thus coextensive with the term "comprising." That is, a first solid-phase support that is "associated with" a first member of FRET pair can "comprise" the first member of the FRET pair. Similarly, a first solid-phase support that is "associated with" a target-selective binding agent can "comprise" the target-selective binding agent.

Other features and advantages of the disclosure will be apparent from the following description, from the drawings, and from the claims.

DETAILED DESCRIPTION

Figure 1:
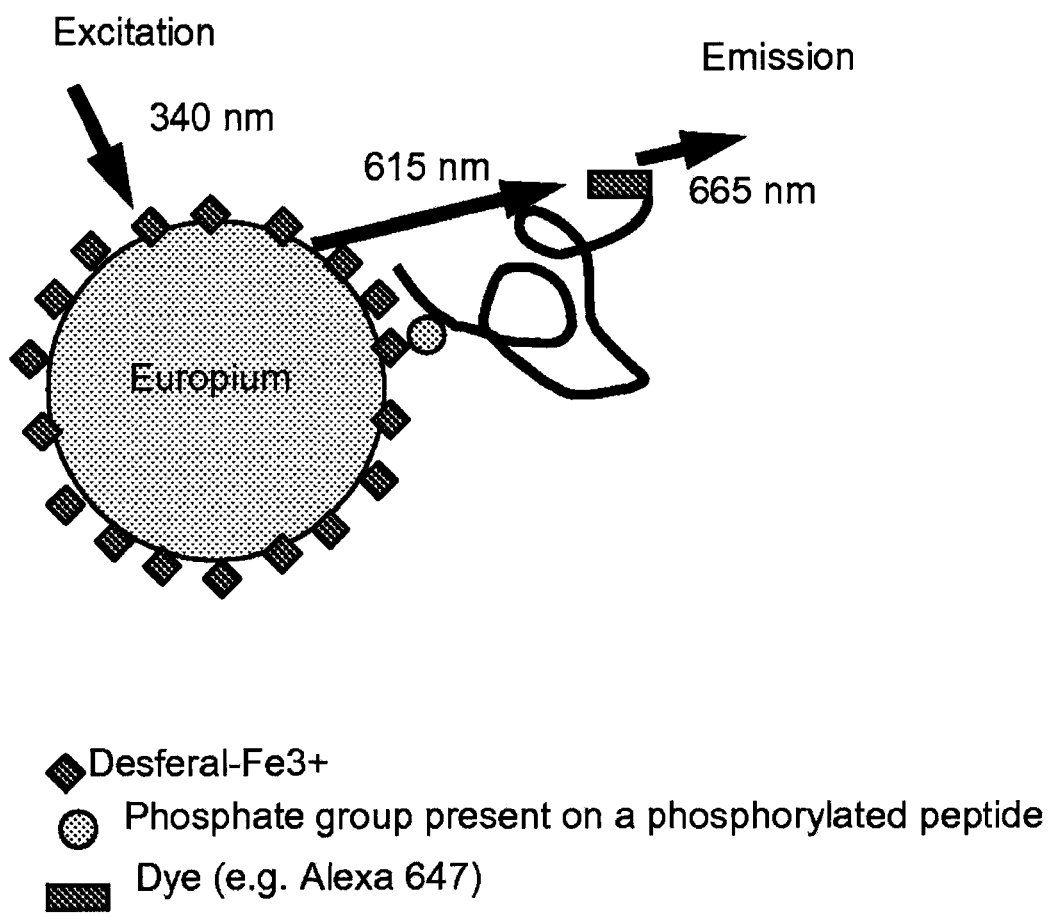
FIG. 1 is schematic diagram of an exemplary composition and method described herein. The shaded diamonds represent Desferal-Fe3+ (a target-selective binding agent) associated with a solid-phase support particle containing a europium chelate as the first member of a FRET pair (and the FRET donor). The small shaded circle represents a phosphate group present on a phosphorylated peptide (a target molecule). The shaded rectangle represents a fluorescent dye (such as ALEXA FLUOR® 647 dye) which is associated with (e.g. covalently linked to) the target molecule. The europium chelate is excited by a light emission of 340 nm and emits light at 615 nm. The dye is then excited by the 615 nm light emission and emits a light signal at 665 nm.

The present disclosure features a variety of compositions and methods useful for, inter alia, detecting and/or analyzing an interaction between two molecules, a target molecule and a target-selective binding agent. The target molecule and target-selective binding agents can be any types of molecules, e.g., proteins, nucleic acids, saccharides or polysaccharides, small molecules, or combinations of any of the foregoing. The methods and compositions can also be used, e.g., to detect the presence or absence of an enzymatic activity (e.g., a kinase activity, a protease activity, or a phosphatase activity) in a sample, to screen for compounds that modulate (e.g., inhibit or enhance) an interaction between two molecules; or to identify compounds that modulate the activity of an enzyme. For example, the compositions and methods can be used to identify compounds that inhibit the interaction between a tumor suppressor and an inhibitor of the tumor suppressor (e.g., p53 and MDM2) or the interaction between a viral surface protein (e.g., gp160) and its cognate host cell receptor (e.g., CD4). Such compounds can be useful in the treatment, or in the prevention, of a variety of diseases including cancer, infectious diseases (e.g., viral, bacterial, or protozoan-based infections), immunological disorders, or neurological disorders.

Exemplary compositions and methods embraced by the disclosure are set forth below.

Compositions

The disclosure features compositions comprising: a first solid-phase support associated with a target-selective binding agent and a first member of a Fluorescence Resonance Energy Transfer (FRET) pair. The disclosure also features compositions comprising a target molecule associated with (or comprising) a second member of the FRET pair. In some embodiments, the target molecule is not associated with (e.g., is not covalently or non-covalently bound to) a second solid-phase support. In some embodiments, the second member of the FRET pair is not associated with (e.g., is not covalently or non-covalently bound to) or is not a component of a second solid-phase support. In some embodiments, the compositions do not comprise a radioisotope (e.g., $^{35}S$, $^{32}P$, $^{33}P$, $^{125}I$, or $^{3}H$).

The compositions described herein take advantage of Fluorescence Resonance Energy Transfer (FRET), which entails the radiationless transfer of energy from an excited donor molecule to an acceptor molecule (sometimes referred to herein as a donor/acceptor pair). The FRET donor molecule initially absorbs energy (and is thus excited) and then transfers energy, by way of emission, to the FRET acceptor molecule (resulting in excitation of the FRET acceptor molecule). The resonance energy transfer can occur over distances greater than inter-atomic distances, and without conversion to thermal energy nor any molecular collision. The FRET donor or the FRET acceptor can be selected based on a variety of factors such as stability, excitation, and emission wavelengths as well as signal intensity. For example, the FRET acceptor is generally selected such that it is capable of emitting light when excited by light of the wavelength emitted by the FRET donor. It is understood that FRET includes Time-Resolved FRET (or TR-FRET), which combines the use of long-lived fluorophores and time-resolved detection (a delay between excitation and emission detection) to minimize fluorescent interference due to any inherent fluorescence of, e.g., target molecules or target-selective binding agents (see, e.g., Klostermeier et al. (2001-2002) Biopolymers 61(3):159-79). Examples of long-lived fluorophores include, e.g., lanthanide chelates (see below).

In some embodiments, the first member of the FRET pair is the FRET donor and the second member of the FRET pair is the FRET acceptor. In some embodiments, the second member of the FRET pair can be the FRET donor and the first member of the FRET pair is the FRET acceptor.

In some embodiments, the first member of the FRET pair and/or the second member of the FRET pair can be fluorescent. The first and/or second member of the FRET pair can be, e.g., a fluorescent dye such as, but not limited to, an Alexa dye, an allophycocyanin (APC) dye, a carboxyfluorescein dye, a tetramethyl-6-carboxyrhodamine (TAMRA) dye, a HiLyte™ Fluor dye (e.g., HiLyte™ Fluor 488 Dye, 555 Dye, 647 Dye, 680 Dye, 750 dye; Anaspec), a cyanine dye (e.g., Cy3 or Cy5), or a dye selected from the group consisting of DY-415, DY-547, DY-590, DY-634, DY-682, and DY-505 (Dyomics GmbH, Germany). The fluorescent dyes can include all fluorescent dyes capable of emitting light of at least 520 nm or above.

In some embodiments, the first member or the second member of the FRET pair can be, or comprise, a lanthanide chelate. As described below, lanthanide chelates are characterized by long fluorescence decay after excitation (up to a millisecond), which allows time-delayed signal detection to reduce background signal originating, for example, from sample component, and large Stokes shifts, which reduces crosstalk, resulting in high signal-to-background ratios. A variety of lanthanide chelates have been described and are commercially available. Exemplary lanthanide chelates include, e.g., DELFIA®, LANCE®, and TruPoint™ lanthanide chelates (PerkinElmer, Boston, Mass.); "TEKES" (4-(4-isothio-cyanatophenylenthynyl-2,6-{N,N-bis(carboxymethyl)aminomethyl]-pyridine)-based lanthanide chelates; ethylenediamine tetraacetic acid (EDTA)-based lanthanide chelates; DTPA-based lanthanide chelates (see, e.g., BioPhysics Assay Laboratory Inc., Worcester, Mass.); DOTA-based lanthanide chelates; DOPTA-based lanthanide chelates; europium cryptate (Cisbio, Bedford, Mass.); a diketonate family chelate (e.g., b-diketonate chelates; see, e.g., Voloshin et al. (2001) J Luminescence 93(2):115-118; Song et al. (2003) J Crystal Growth 250(3):423-430; and Ribeiro et al. (2007) J Brazilian Chemical Society 18(2)); or any LanthaScreen™ lanthanide chelates (Invitrogen, Carlsbad, Calif.). Exemplary lanthanides include, e.g., europium, terbium, samarium, and dysprosium.

Figure 2:
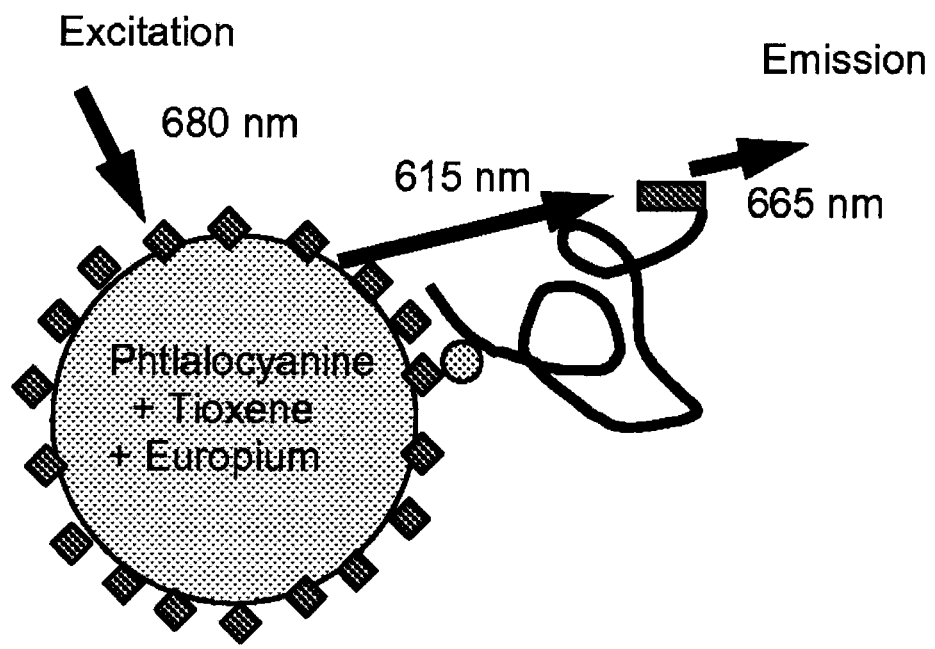
FIG. 2 is schematic diagram of an exemplary composition and method described herein. The shaded diamonds represent Desferal-Fe3+(the target-selective binding agent) associated with a solid-phase support particle containing a europium chelate as the first member of a FRET pair (and the FRET donor). The particle also contains phthalocyanine and thioxene. The small shaded circle represents a phosphate group present on a phosphorylated peptide (target molecule). The shaded rectangle represents a fluorescent dye (such as ALEXA FLUOR® 647 dye) which is associated with the target molecule. In this case, a light emission of 680 nm excites phthalocyanine, which in turn produces singlet oxygen from ambient oxygen. The singlet oxygen is capable of activating thioxene, which then emits light at 340 nm. The europium chelate is excited by a light emission of 340 nm and emits light at 615 nm. The dye is then excited by the 615 nm light emission and emits a light signal at 665 nm.

In FIGS. 1 and 2, the exemplary moiety capable of emitting light is a lanthanide chelate, such as a europium chelate. For this exemplary fluorophore, the emission wavelength is longer than the excitation wavelength.

In some embodiments, the first solid-phase support can contain one or more reagents capable of activating the FRET donor. For example, the first solid-phase support can contain (i) a reagent that can generate singlet oxygen; and (ii) a reagent that emits light when it is exposed to (or interacts with or reacts with) singlet oxygen. An example of such a pair of reagents is phthalocyanine (i) and thioxene (ii) (see, e.g., FIG. 2). Other reagents capable of generating singlet oxygen include, e.g., methylene blue; rose bengal; a porphyrin; 9-alkylidene-N-alkyl acridans; enolethers; enamines; 9-alkylidene xanthenes; and endoperoxides such as such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide (see, e.g., U.S. Pat. No. 6,251,581). Heating or direct absorption of light by some of these compounds releases singlet oxygen (see, e.g., Kanofsky et al. (1983) J Biol. Chem. 259:5596 and PCT Publication No. WO 01/84157, the disclosure of each of which is incorporated by reference in their entirety). Additional reagents capable of producing a light emission upon interaction with singlet oxygen include, e.g., olefins (see, e.g., U.S. Pat. Nos. 5,709,994 and 6,251,581; European Patent Application No. 0345776; and WO 01/84157, supra, the disclosures of each of which are incorporated herein by reference in their entirety).

The target molecules and target-selective binding agents described herein can be (or can comprise) any of a variety of molecule types including, e.g., biomolecules. For example, the target molecules and target-selective binding agents can be, or contain, a polypeptide (e.g., a short peptide; a large protein such as a nucleic acid binding protein or an enzyme; or a macromolecular complex such as an antibody or target-selective binding fragment thereof), a nucleotide (e.g., ribonucleotide or deoxynucleotide) or polynucleotide, a saccharide or polysaccharide, a lipid, a small molecule, or any combination of the foregoing. Examples of target-selective binding agents include, e.g., antibodies or antigen-binding fragments thereof, antibody-like molecules, aptamers, receptors, ligands, proteins, nucleic acids, or metal ions and/or chelates thereof. An antibody or antigen-binding fragment thereof can be, e.g., a monoclonal antibody, a polyclonal antibody, a chimeric antibody, a humanized antibody, a fully human antibody, a single chain antibody, an $F_{ab}$ fragment, an $F_{(ab')2}$ fragment, an $F_{ab'}$ fragment, an $F_v$ fragment, or an $scF_v$ fragment. In some embodiments, the target-selective binding agent or target molecule is not an antibody or antigen-binding fragment thereof.

A variety of polypeptides can be used as target molecules or target-selective binding agents such as, but not limited to, microbial polypeptides (e.g., viral, bacterial, or protozoan polypeptides), enzymes, disease markers (such as polypeptide cancer antigens), cell surface receptors, hormone receptors, cytokines, chemokines, tissue specific antigens, or fragments of any of the foregoing.

Polynucleotides can vary in size. For example, a polynucleotide can be about 10 (e.g., 15, 20, 25, 30, 35, 40, 45, 50, 55, 60, 65, 70, 75, 80, 85, 90, 95, 100, 110, 120, 150, 200, 300, 400, 500, 1000, 2000, 5000, 10000, 20000, 40000, or 50000) or more nucleotides. The polynucleotides can include nucleic acids from any source in purified or unpurified form, naturally occurring or synthetically produced, including DNA and RNA, or can be t-RNA, m-RNA, r-RNA, mitochondrial DNA and RNA, chloroplast DNA and RNA, DNA-RNA hybrids, or mixtures of any of the foregoing. Polynucleotides can be single stranded or double-stranded and can contain both double-stranded and single-stranded regions.

The target molecules or target-selective binding agents can be obtained from a natural source (such as a cell sample, a tissue sample, or an extract thereof) or can be synthetic or recombinant. For example, a target molecule such as an antibody, a transcription factor, or a polynucleotide, can be purified from a natural cellular source using any of a variety of methods known in the art (see, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated by reference in its entirety). Smaller target molecules or target-selective binding agents, e.g., polypeptide or nucleic acid target molecules or target-selective binding agents having less than 200 (e.g., less than 175, less than 150, less than 125, less than 100, less than 90, less than 80, less than 70, or less than 60) amino acids or nucleotides can be chemically synthesized by standard chemical means.

Suitable methods for constructing nucleic acids and expression vectors for recombinant expression of target molecules or target-selective binding agents (e.g., nucleic acid or polypeptide molecules or agents) are well known to those skilled in the art and described in, e.g., Sambrook et al. (supra).

A recombinant nucleic acid can be introduced into a cell using a variety of methods, which methods can depend, at least in part, on the type of cell into which the nucleic acid is introduced. For example, bacterial cells can be transformed using methods such as electroporation or heat shock. Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., supra).

Expression systems that may be used for small or large scale production of the target-selective binding agents described herein include, but are not limited to, microorganisms such as bacteria (for example, *E. coli* and *B. subtilis*); yeast (for example, *Saccharomyces* and *Pichia*); insect cell systems; plant cell systems; or mammalian cell systems (for example, COS, CHO, BHK, 293, VERO, HeLa, MDCK, WI38, and NIH 3T3 cells).

Following the expression of any of the recombinant target molecules or target-selective binding agents described herein, the recombinant molecules or agents can be isolated from the cultured cells, or from the media in which the cells were cultured, using standard techniques (see Sambrook et al., supra). Methods of isolating target molecules or target-selective binding agent (e.g., proteins and nucleic acids) are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Choice of a particular target-selective binding agent can depend on, e.g., the nature of the assay and the materials available for selectively binding to a particular target molecule. For instance, when the target molecule is a phospho-molecule, examples of suitable target-selective binding agents include an anti-phosphotyrosine antibody, anti-phosphoserine antibody, anti-phosphothreonine antibody, a phosphoaffinity material containing a siderophore/metal ion complex and a hydrated metal oxide. In the specific examples depicted in FIGS. 1 to 3, the target-selective binding agent is a phosphoaffinity material containing Desferal® (also known as desferrioxamine, desferoxamine, DFO, DFOA, or deferoxamine; N'-[5-(acetyl-hydroxy-amino)pentyl]-N-[5-[3-(5-aminopentyl-hydroxy-carbamoyl)propanoylamino]pentyl]-N-hydroxy-butane diamide) chelated with $Fe^{3+}$.

In some embodiments, a target molecule can be of the same molecule type as the target-selective binding agent. For example, a target molecule can be a polypeptide and the target-selective binding agent can also be a polypeptide. In some embodiments, a target molecule can be of one molecule type and the target-selective binding agent of another molecule type. For example, a target molecule can be a nucleic acid and the target selective binding agent can be a polypeptide or vice versa. All that is required is that the target-selective binding agent bind to the corresponding target molecule or vice versa.

A target-selective binding agent can preferentially bind to one form of a target molecule over another. That is, the target-selective binding agent can preferentially bind to, e.g., an unmodified target molecule as compared to the binding of the target-selecting binding agent to a modified target molecule. For example, the binding of a target-selective binding agent can be inhibited by a modification of the target molecule such as phosphorylation, glycosylation, ubiquitination, or any other modifications described herein. In one instance, the interaction between an antibody (used as a target-selective binding agent) and a target molecule can be disrupted when the target molecule is glycosylated (e.g., a glycosylated form of viral surface antigen).

In some embodiments, the target-selective binding agent can preferentially bind to a modified target molecule as compared to the binding of the target-selecting binding agent to an unmodified target molecule. For example, the binding of a target-selective binding agent can be enhanced by a modification of the target molecule. That is, e.g., a src-homology 2 (SH2) domain (used as a polypeptide target-selective binding agent) can preferentially bind to a polypeptide target molecule that is phosphorylated, but have a lower affinity for a non-phosphorylated form of the polypeptide target molecule.

It is understood that use of the terms "target-selective binding agent" and "target molecule" herein does not imply a unidirectionality of binding. Rather, the terms are used only to represent two members of a binding pair. Thus, in some circumstances, one member may bind the other, while in other cases both members exhibit some binding for the other member.

A target-selective binding agent and/or target molecule can be, and/or be capable of being, modified in a variety of ways. Suitable types of modification will vary, e.g., on the nature of the target molecule or target-selective binding agent and include, e.g., phosphorylation, glycosylation, ubiquitination, methylation, SUMOlyation, acetylation, sulfation, ligation, or prenylation. Types of moieties that can be added to a target molecule or target-selective binding agent, include, but are not limited to, a phosphomonoester moiety, a saccharide moiety, a ubiquitin moiety, an acetyl moiety, a SUMO moiety, a farnesyl moiety, and a geranyl-geranyl moiety.

Modifications of target-selective binding agents and/or target molecules can also include those modifications that remove a portion of a target molecule or a target-selective binding agent such as modifications by a protease (for proteins) or by nuclease (for nucleic acids). For example, a portion of a polypeptide target molecule or polypeptide target-selective binding agent can be removed through the action of a protease, thus modifying the target molecule or target-selective binding agent. In another example, a portion of a polynucleotide target molecule (or target-selective binding agent) that is single-stranded can be removed by Mung bean nuclease.

A second member of a FRET pair can be, e.g., covalently bound to a target molecule or can be connected to the target molecule by way of a first and second member of a binding pair. For example, a target molecule can be bound to biotin (or a functional or structural equivalent thereof), and the second member of the FRET pair bound to streptavidin (or avidin, or functional or structural equivalent thereof). Suitable methods for binding a second member of a FRET pair to a target molecule depend on, e.g., the nature of the target molecule (e.g., a protein, a nucleic acid, or a small molecule) and the nature of the second member that is to be attached, and are known in art (see, e.g., Peloquin et al. (2004) Nature Methods 2(4):1; Hermanson (1996) Bioconjugate Techniques, Academic Press, New York; Haugland RP (1995) Methods Mol Biol 45: 205-21; Brinkley M (1992) Bioconjug Chem. 3: 2-13; and Banks et al. (1995) Bioconjug Chem. 6: 447-58). A variety of target molecules that are bound to a second member of a FRET pair (e.g., a fluorophore) are commercially available from, e.g., Invitrogen (Carlsbad, Calif.) and Santa Cruz Biotechnology (Santa Cruz, Calif.). In addition, commercial kits are available for conjugating a second member of a FRET pair to a target molecule (e.g., Anaspec, San Jose, Calif.).

As used herein, the term "solid-phase support" refers to any solid or semi-solid material to which a target-selective binding agent can be attached or incorporated (e.g., physical entrapment, adsorption, etc.) or which can be functionalized to include (e.g., to associate with) a target-selective binding agent. In addition to a first member of a FRET pair (or a target selective binding agent), a solid-phase support can contain a variety of materials including, e.g., a natural or synthetic polymer, resin, metal, or silicate. Suitable solid-phase supports are known in the art and illustratively include an agarose (commercially available as SEPHAROSE® agarose); a cellulose (e.g., a carboxymethyl cellulose); a dextran, (such as SEPHADEX® dextran); a polyacrylamide; a polystyrene; a polyethylene glycol; a resin; a silicate; divinylbenzene; methacrylate; polymethacrylate; glass; ceramics; paper; metals; metalloids; polyacryloylmorpholide; polyamide; poly(tetrafluoroethylene); polyethylene; polypropylene; poly(4-methylbutene); poly(ethylene terephthalate); rayon; nylon; poly (vinyl butyrate); polyvinylidene difluoride (PVDF); silicones; polyformaldehyde; cellulose acetate; nitrocellulose, or combinations of two or more of any of the foregoing. All that is required is that the material or combination of materials in the solid-phase support not interfere, or in some cases only minimally interfere, with the FRET between the first and second members of the FRET pair and/or the binding between the target molecule and target-selective binding agent (or where applicable, the reagents capable of exciting the FRET donor (such as through generation of singlet oxygen).

A solid-phase support can have a variety of physical formats, which can include for example, a membrane; a chip (e.g., a protein or nucleic acid chip); a slide (e.g., a glass slide or coverslip); a column; a hollow, solid, semi-solid, pore or cavity containing particle such as a bead; a gel; a fiber including a fiber optic material; a matrix; and a sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. A particle to which a target-selective binding agent is associated with can have a variety of sizes, including particles that remain suspended in a solution of desired viscosity, as well as particles that readily precipitate in a solution of desired viscosity. Particles can be selected for ease of separation from sample constituents, for example, by including purification tags for separation with a suitable tag-binding material, paramagnetic properties for magnetic separation, and the like.

In some embodiments, the solid-phase support (e.g., a particle) can contain a magnetic metal such as magnetite ($Fe_3O_4$), maghemite ($\gamma Fe_2O_3$), or greigite ($Fe_3S_4$) in addition to the first or second member of the FRET pair. The support (e.g., particle) can be superparamagnetic or single-domain (i.e., with a fixed magnetic moment). In some embodiments, the solid-phase support (e.g., particles) can contain non-magnetic metals (e.g., gold or silver) or any of a variety of metal salts (e.g., cadmium sulfide). The particles can contain one or more (e.g., two three, four, five, six, seven, eight, nine, 10, 11, 12, 13, 14, 15, 20, 25, 30, or more) of any of the above-described suitable materials.

Generally, a particle described herein has a spherical shape. However, a particle can be, e.g., oblong or tube-like. In some embodiments, e.g., a crystalline form particle, the particle can have polyhedral shape (irregular or regular) such as a cube shape. In some embodiments, a particle can be amorphous.

In some embodiments, the particle or particle mixture can be substantially spherical, substantially oblong, substantially tube-like, substantially polyhedral, or substantially amorphous. By "substantially" is meant that the particle, or the particle mixture, is more than 30 (e.g., 35, 40, 45, 50, 55, 60, 65, 70, 75, 80, 85, 90, 95, 96, 97, 98, or 99 or more) % of a given shape.

In some embodiments, the diameter (or longest straight dimension) of the particle can be between about 1 nm to about 1000 nm or larger. For example, a particle can be at least about 1 nm to about 1000 nm (e.g., at least about two, three, four, five, six, seven, eight, nine, 10, 15, 20, 25, 30, 35, 40, 45, 50, 75, 100, 150, 200, 250, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm). In some embodiments, a particle can be not more than 1000 nm (e.g., not more than 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 225, 200, 175, 150, 125, 100, 75, 50, 45, 40, 35, 30, 25, 20, 15, 10, or five nm) in diameter (or at its longest straight dimension).

In some embodiments, the solid-phase support can contain arrays of two or more different target-selective binding agents. In some embodiments, an array can include target-selective binding agents (of a plurality of target-selective binding agents) immobilized at predetermined positions such that each different target-selective binding agent can be identified by its position. The solid-phase support arrays can have two or more (e.g., three or more; four or more; five or more; six or more; seven or more; eight or more; nine or more; 10 or more; 11 or more; 12 or more; 13 or more 14 or more; 15 or more; 16 or more; 17 or more; 18 or more; 19 or more; 20 or more; 21 or more; 22 or more; 23 or more; 24 or more; 25 or more; 30 or more; 35 or more; 40 or more; 42 or more; 45 or more; 47 or more; 50 or more; 52 or more; 55 or more; 57 or more; 60 or more; 62 or more; 65 or more; 67 or more; 70 or more; 75 or more; 80 or more; 85 or more; 90 or more; 95 or more; 100 or more; 150 or more; 200 or more; 300 or more; 400 or more; 500 or more; 600 or more; 1,000 or more; 2,000 or more; 5,000 or more; 10,000 or more; 20,000 or more; 30,000 or more; 50,000 or more; or 100,000 or more) different target-selective binding agents. In some embodiments, the solid-phase support can contain arrays having can have less than 100,000 (e.g., less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, less than 90, less than 80, less than 70, less than 60, less than 55, less than 50, less than 45, or less than 40) different target-selective binding agents.

Suitable methods for producing solid-phase supports, as well as additional examples of solid-phase supports (e.g., particles) for use in the compositions and methods described herein, can be found in, e.g., PCT Publication Nos. WO 01/84157, WO 99/30160, WO 99/42838, and WO 06/078618, the disclosures of each of which are incorporated by reference in their entirety.

In some embodiments, encoded particles can be used. For example, compositions comprising two or more first solid-phase support particles, wherein at least two of the first particles are bound to different target-selective binding agents. Such encoding can allow a mixture of first solid-phase supports to be separated, however, such encoding should not, or only minimally, interfere with FRET between the first and second member of the FRET pair and/or the binding between the target molecule and the target-selective binding agent (or where applicable, the activity of the one or more reagents capable of exciting the first member of the FRET pair). Each particle includes a unique code, and like the above-described arrays, all target-selective binding agents (of a plurality of target-selective binding agents) are identifiable by a particular code. The code can be provided by any detectable means, such as by holographic encoding, by a fluorescence property, color, shape, size, weight, light emission, quantum dot emission and the like to identify particle and thus the capture probes immobilized thereto. Encoding can also be the ratio of two or more dyes in one particle that is different than the ratio present in another particle. For example, the particles may be encoded using optical, chemical, physical, or electronic tags. Examples of such coding technologies are optical bar codes fluorescent dyes, or other means. In some embodiments, the particle code is a nucleic acid, e.g., a single stranded nucleic acid. For example, a first solid-phase support particle can be attached to a single- or double-stranded nucleic acid, each strand being about 10 nucleotides (e.g., about 15 nucleotides, about 20 nucleotides, about 25 nucleotides, about 30 nucleotides, about 35 nucleotides, about 40 nucleotides, about 50 nucleotides, about 75 nucleotides, about 100 nucleotides, or about 150 or more nucleotides) in length.

Different encoded particles can be used to, e.g., evaluate in parallel (i) a number of different enzymatic activities or (ii) a number of different target-selective binding agents, so long as the encoding can be used to identify a particular target-selective binding agent on a particular particle.

One exemplary platform utilizes holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

A target-selective binding agent can be associated with a first solid-phase support in a number of ways. For example, the target-selective binding agent can be covalently or non-covalently bound to a first solid-phase support.

A variety of chemical reactions useful for covalently attaching a substrate to a support are well known to those skilled in the art (see, for example, Hartmann et al. (2002) J. Mater. Res. 17(2):473-478). Illustrative examples of functional groups useful for covalent attachment of substrates to a support include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity. Illustrative examples of binding partners useful for non-covalent attachment of substrates to a support include antibodies, antibody-like materials, and agents, e.g., that are capable of binding to antibodies such as, but not limited to, staphylococcal protein A or protein G.

In some embodiments, the surface of the solid-phase support can be modified to facilitate the stable attachment of linkers or binding agents. Generally a skilled artisan can use routine methods to modify a solid-phase support in accordance with the desired application. The following are non-limiting examples of solid-phase support modifications.

The surface of the solid-phase support can, e.g., have a coating that facilitates the attachment to the target-selective binding agent. In general, the coating will be one that is complementary to a linker moiety on the target-selective binding agent. For example, the coating on the solid-phase support can be biotin and the target-selective binding agent can be bound to streptavidin.

The surface of a solid-phase support can be amidated, e.g., by silylating the surface, e.g., with trialkoxyaminosilane. Silane-treated supports can also be derivatized with homobifunctional and heterobifunctional linkers. The support can be derivatized, e.g., so it has a hydroxy, an amino (e.g., alkylamine), carboxyl group, N-hydroxy-succinimidyl ester, photoactivatable group, sulfhydryl, ketone, or other functional group available for reaction. The supports can be derivatized with a mask in order to only derivatize limited areas (e.g., certain wells of a multiwell assay plate) or a chemical etch or UV light can be used to remove derivatization from selected regions.

The functional groups, instead of being coated on the surface, can be incorporated into the first solid-phase support either during or after the preparation of the first solid-phase support. The functional groups are usually chosen to dissolve in one or more components of the first solid-phase support but may be covalently attached to the first solid-phase support (as described above).

Additional methods for attaching a target-selective binding agent to a solid-phase support are described in, e.g., PCT Publication Nos. WO 01/84157, WO 99/30160, and WO 06/078618, the disclosures of each of which are incorporated by reference in their entirety.

The first member of the FRET pair can be associated with the first solid-phase support in a variety of ways. For example, the first solid-phase support can comprise the first member of the FRET pair (e.g., all or part of the solid-phase support can be made up of the first member of the binding pair or the first member of the FRET pair can be adsorbed onto the solid-phase support). In another example, the first member of the FRET pair can be covalently or non-covalently bound to the first solid-phase support. In yet another example, the first member of the FRET pair can be covalently or non-covalently bound to the target-selective binding agent, which agent can be covalently or non-covalently bound to the solid-phase support. For example, a target-selective binding agent can be bound to biotin (or a functional or structural equivalent thereof), and the first member of the FRET pair bound to streptavidin (or avidin, or functional or structural equivalent thereof). Suitable methods for binding a first member of a FRET pair to a target-selective binding agent depend on, e.g., the nature of the target-selective binding agent e.g., a protein, a nucleic acid, a carbohydrate, or a small molecule) and the nature of the first member of the FRET pair that is to be attached, and are described above.

In some embodiments, the compositions can include at least two (e.g., three, four, five, six, seven, eight, nine, 10, 15, 20, 25, 30, 35, 40, 45, or 50 or more) first solid-phase supports, at least two of which associated with a different target-selective binding agents. For example, a composition can include one first solid-phase support associated with a first form of a kinase substrate and another first solid-phase support associated with a second form of a kinase substrate. The at least two first solid-phase supports can be separated from one another (e.g., in different wells of a multi-well assay plate) or can be in different locations on a larger support structure (e.g., each of the first solid-phase support in a separate well of a multi-well assay plate). The at least two first solid-phase supports can, alternatively, be in a mixture. In embodiments where the at least two solid-phase support are in a mixture and are particles, the solid-phase support particles can be encoded particles (see above).

In some embodiments, the compositions can include a mixture of first solid-phase supports, wherein the mixture includes two or more (e.g., three, four, five, six, seven, eight, nine, 10, 11, 12, 13, 15, 20, 22, 25, 27, 30, 32, 35, 40, or 45 or more) pluralities of first solid-phase supports, at least two of the two or more pluralities comprising first solid-phase supports associated with different target-selective binding agents, and wherein the first solid-phase supports comprise a first member of a Fluorescence Resonance Energy Transfer (FRET) pair; and a target molecule comprising a second member of the FRET pair. In some embodiments, the target molecule is not associated with a second solid-phase support.

In embodiments where the particles are in a dispersion of a plurality of first solid-phase particles, the size distribution can have a standard deviation of no more than about 35% (e.g., one, two, three, four, five, six, seven, eight, nine, 10, 15, 20, 25, 30, or 35%) of the average diameter of the plurality of particles.

In some embodiments, the compositions described herein can be frozen, lyophilized, or immobilized and stored under appropriate conditions, which allow the target-selective binding agents and target molecules and the first and second members of the FRET pair to retain activity. In some embodiments the compositions can be in a suspension or slurry and/or can include one or more aqueous solutions (e.g., buffers) for suspending the compositions.

Figure 3:
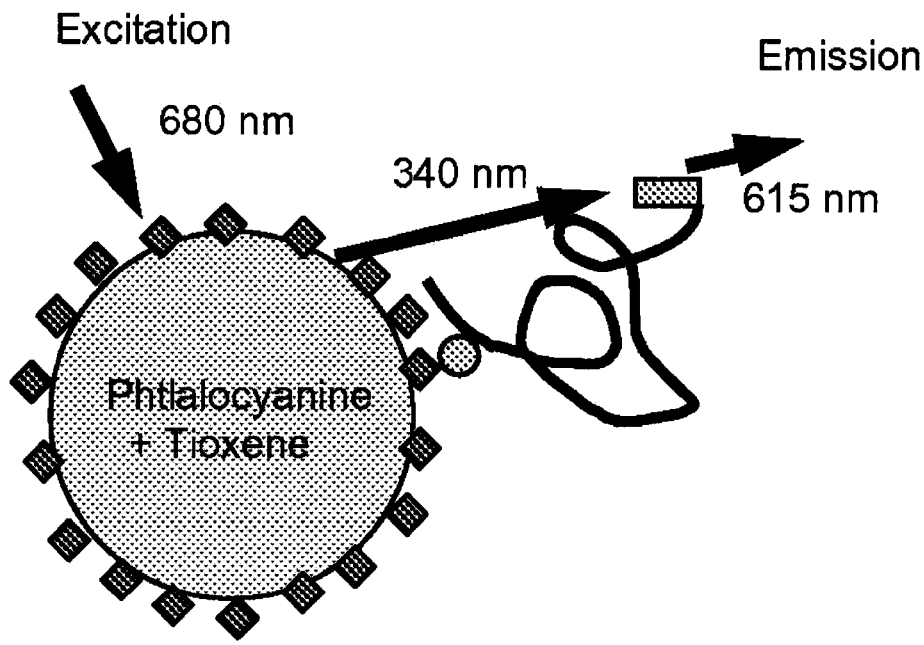
FIG. 3 is schematic diagram of an exemplary composition and method described herein. The shaded diamonds represent Desferal-Fe3+(the target-selective binding agent) associated with a solid-phase support particle containing phthalocyanine (a source of singlet oxygen) and thioxene (the first member of a FRET pair and a FRET donor). The small shaded circle represents a phosphate group present on a phosphorylated peptide (target molecule). The shaded rectangle represents a europium chelate which is associated with the target molecule. In this case, a light emission of 680 nm excites phthalocyanine, which in turn produces singlet oxygen from ambient oxygen. The singlet oxygen is capable of activating thioxene, which then emits light at 340 nm. The europium chelate is excited by a light emission of 340 nm and emits light at 615 nm.

Exemplary compositions are set forth in FIGS. 1, 2, and 3.

Applications

The technology described herein relates, in part, to detecting interactions between at least two molecules—a target molecule and a target-selective binding agent. Generally, the methods involve the use of (i) a first solid-phase support such as a particle or suitable solid surface associated with a target-selective binding agent and a first member of a FRET pair and (ii) a target molecule associated with a second member of the FRET pair. In such methods, which are described below in more detail, interaction of the target molecule with the target-selective binding agent associated with the first solid-phase support results in the generation of a detectable light signal. The light signal is measured as a read-out of the presence or amount of the target molecule associated with the target-selective binding agent associate with the first solid-phase support. The light signal can be, e.g., light emission from the target molecule, which is generated when the second member of the FRET pair (in this case a FRET acceptor) becomes excited by an emission from the first member of the FRET pair (in this case being the FRET donor). It is understood that in some embodiments this stimulation process can work in the reverse direction. For example, an emission from an excited second member of the FRET pair (in this case the FRET donor) can in turn excite the first member of the FRET pair (in this case being the FRET donor) associated with the first solid-phase support. Various exemplary reaction schemes by which the first or second member of the FRET pair can be stimulated to emit light signals are described below.

High concentrations of the target-selective binding agent on the surface of the first solid-phase support allow for increased avidity for the target molecule. Thus, the methods described herein can exhibit increased sensitivity where, e.g., low concentrations of target molecule are present. In addition, the methods described herein can be performed without the need or aid of radioisotopes.

In accordance with the above-described compositions, a method to detect a target molecule of interest, e.g., a modified target molecule such as a phosphorylated molecule, or a method to detect or analyze the interaction between a target molecule and a target-specific binding agent, is carried out as follows. A sample containing a target molecule associated with a second member of a FRET pair is contacted with the first solid-phase support associated with a first member of a FRET pair. An interaction between the target molecule and the target-selective binding agent can be detected by first exciting the first member of the FRET pair with light. This light excites the first member of the FRET pair, which in turn emits light at a wavelength capable of exciting the second member of the FRET pair. The excited second member of the FRET pair then emits a light signal that is detected by a detector. The presence or amount of the light signal emitted by the second member of the FRET pair indicates the presence or amount of target molecule associated with the target-selective binding agent on the first solid-phase support. Alternatively, where the second member of the FRET pair is the FRET donor and the first member of the FRET pair is the FRET acceptor, the interaction between the target molecule and the target-selective binding agent can be determined by detecting the presence or amount of light emission from the first member of the FRET pair. That is, the second member of the FRET pair can be excited by light (e.g., light produced from a laser), which in turn emits light at a wavelength capable of exciting the first member of the FRET pair.

In one exemplary assay configuration, a method to detect a phosphomolecule (or the interaction between a phosphomolecule and a phosphomolecule binding agent), as shown in FIG. 1, is carried out as follows. A sample is contacted with a first solid-phase support (in this case assay beads) containing a europium chelate (which is physically incorporated in the beads). The assay beads also incorporate Desferal™ binding agent (see above); Desferal is a phosphate-specific binding agent. After contacting, a phosphomolecule comprising a second member of the FRET pair contained in the sample comes into close proximity with the assay bead. The europium chelate is excited with applied light at 340 nm and then emits light at 615 nm, which in turn excites an acceptor dye (e.g. ALEXA FLUORO® 647 dye or another dye excitable in the 600 nm range) that is associated with the phosphomolecule. Following excitation, the acceptor dye (ALEXA FLUORO® 647 dye) emits light at 665 nm. The light is then detected and correlated with the presence or amount of phosphomolecule in the sample.

In another exemplary assay configuration shown in FIG. 2, the assay bead contains, in addition to a first member of the binding pair capable of emitting light (the FRET donor; in this case a Europium chelate), a reagent capable of producing singlet oxygen in response to light stimulation (phthalocyanine) and a dye that emits light in response to singlet oxygen (thioxene). In the assay format exemplified by FIG. 2, upon light excitation at 680 nm, the phthalocyanine will transform ambient oxygen into singlet oxygen that will activate the thioxene which in turn excites the europium chelate. The excited europium chelate will then emit light at 615 nm that in turn excites an acceptor dye associated with the target molecule (e.g. ALEXA FLUOR® 647 dye or another dye excitable in the 600 nm range). Following excitation, the acceptor dye (ALEXA FLUOR® 647 dye) emits light at 665 nm. The 665 nm emission is then detected and correlated with the presence or amount of target molecule (e.g., phosphomolecule) in the sample.

Another exemplary assay configuration shown in FIG. 3 involves using europium chelate as the FRET acceptor dye, instead of the donor dye. The assay bead contains phthalocyanine and thioxene only. Upon excitation at 680 nm, the phthalocyanine will transform ambient oxygen into singlet oxygen that will activate the thioxene, which emits light at 340 nm. This secondary light source is used as a donor. A Europium chelate-labeled target molecule is excited by this light and will emit at 615 nm. The 615 nm emission is then detected and correlated with the presence or amount of target (e.g., phosphomolecule) in the sample and the binding between the target and target-selective binding agent (e.g., phosphomolecule and the phosphomolecule binding agent).

In some embodiments, the amount of interaction between a target-selective binding agent and the target molecule can be determined as a ratio of the emission of the FRET acceptor to the emission of the FRET donor (FRET donor/FRET acceptor). For example, the presence or amount of interaction between the target molecule and target-selective binding agent depicted in FIG. 1 can be determined as a ratio of the FRET615/FRET665 emissions.

Although FIGS. 1, 2 and 3 depict assay formats using beads, a variety of solid surfaces, such as microplates, sample vessels, wells and the like, can be employed in the methods described herein. Similarly, although the Figures depict using Europium chelate and a dye (when applicable), any other fluorophore, dye and combinations thereof, having suitable excitation and emission wavelengths (see above) can be employed in the methods described herein.

The methods for detecting interactions can be used to, e.g., determine the target specificity for a particular target-selective binding agent or vice versa. For example, the methods can be used to determine the binding specificity of a nucleic acid binding protein such as a transcription factor (e.g., a zinc finger protein). In such embodiments, the methods can employ compositions that include at least two (e.g., three, four, five, six, seven, eight, nine, 10, 15, 20, 25, 30, 35, 40, 45, or 50 or more) first solid-phase supports, at least two of which are associated with a different target-selective binding agents. For example, one first solid-phase support can be associated with a first nucleic acid sequence and another first solid-phase support can be associated with a second nucleic acid sequence. Each of the first and second nucleic acid sequences can be contacted with a nucleic acid binding protein target-molecule.

The methods can, and may generally, be earned out in an aqueous buffered medium at a physiological pH. However, any of a variety of conditions can be employed that provide acceptable assay sensitivity (that is, acceptable binding between the target-selective binding agent and the target molecule, acceptable activity for an enzyme, and/or acceptable FRET between the first and second member of the FRET pair). The pH for the medium can be in the range of about 4 to 13 (e.g., about 5 to 10 or about 6.5 to 9.5). The pH is generally selected to achieve acceptable assay sensitivity and specificity. Among the factors that must be considered are the pH dependence of the rates of the reactions involved, the binding of binding members and the minimization of non-specific binding, and so forth.

Various buffers may be used to achieve the desired pH and maintain the pH during the determination. Illustrative buffers include borate, phosphate, carbonate, or tris (see, e.g., Sambrook et al., supra).

While the concentrations of the various reagents in the assay medium will generally be determined by the concentration range of interest of the components to be detected, the final concentration of each of the reagents can be determined empirically to optimize the sensitivity of the assay over the range.

Any of a variety of light-emitting and light-detecting instruments can be used to initiate FRET (e.g., excite a FRET donor or excite a reagent capable of exciting the FRET donor) and/or detect an emission produced from said FRET. The light emissions produced by the first and second member of the FRET pair as a result of the above methodologies can be detected or measured visually, photographically, actinometrically, spectrophotometrically, or by any other convenient means to determine the amount thereof, which is related to the amount of each component in the medium. For example, the interaction between a target molecule and a target-selective binding agent can be detected and/or measured using a luminometer.

Specific instruments that can be used in conjunction with the methods and compositions described herein include, e.g., the Victor™, Envision™, Fusion™, and ViewLux™ apparatuses commercially available from PerkinElmer (Boston, Mass.).

In some embodiments, any of the methods described herein can include the step of obtaining the target molecule. For example, where the target molecule is an antibody, the methods can include the step of isolating the antibody from, e.g., a host animal (e.g., a mammal such as a rat, rabbit, mouse, goat, cow, horse, dog, cat, or a human) or cell (e.g., a hybridoma) that produces the antibody. In another example, where the target molecule is a transcription factor, the methods can include the step of isolating the transcription factor from a natural source or obtaining a recombinant transcription factor. Methods for obtaining or isolating a target molecule from natural or recombinant sources are described above in detail as well as in the section entitled "Samples."

In some embodiments, any of the methods described herein can also include the step of conjugating the target molecule to the second member of the FRET pair.

The above-described methods can be used in a variety of applications including, but in no way limited to, the following.

Detecting an Enzymatic Activity

Any of the compositions described herein can be used in various methods for detecting an enzymatic activity in a sample. As aberrant function or expression of any of numerous enzymatic activities (e.g., kinases, phosphatases, or metabolic enzymes such an enzymes involved in the Kreb's cycle) are associated with disease states (such as cancer, inflammatory conditions, or metabolic disorders), the compositions described herein are useful in, e.g., methods for determining whether or not a subject has, or is at risk of developing, a disease characterized by aberrant function or expression of a enzyme.

The methods can include the steps of: contacting one or both of a first solid-phase support associated with a target-selective binding agent and a target molecule with a sample; contacting the target molecule and the first solid-phase support; and detecting binding of the target molecule to the target-selective binding agent. A difference in binding of the target molecule to the target-selective binding agent in the presence of the sample as compared to the binding in the absence of the sample indicates the presence or amount of an enzymatic activity in the sample. The first solid-phase support contains a first member of a Fluorescence Resonance Energy Transfer (FRET) pair and the target molecule is associated with (or comprises) a second member of the FRET pair. In some embodiments, the target molecule is not associated with a second solid-phase support.

The methods can also include the step of covalently or non-covalently binding the second member of the FRET pair to the target molecule and/or covalently or non-covalently binding the target-selective binding agent to the solid-phase support. Methods for covalent or non-covalent binding are described in detail above.

The methods can include the step of, after contacting the target-selective binding agent (associated with the solid-phase support) and the target molecule, separating the solid-phase support from the unbound target molecule. For example, the above method can be conducted in an aqueous buffered medium in a microcentrifuge tube. After the contacting, the solid-phase support suspended in the aqueous medium can be subjected to centrifugation and pelleted at the bottom of the tube. The unbound target molecule can be separated from the pellet along with the aqueous and washed at least once (e.g., twice, three times, or four or more times) to remove any trace amount of unbound target molecule.

A sample can be contacted with a target molecule prior to contacting the target molecule with the target-selective binding agent. A sample can be contacted with the target-selective binding agent prior to contacting the target-selective binding agent and the target molecule. In some embodiments, the target-selective binding agent can be contacted with the target molecule in the presence of the sample (that is, the target molecule and target-selective binding agent are both contacted with the sample at the same time).

Any of a wide variety of enzymatic activities can be detected by the methods described herein. For example, the enzymatic activity can be, e.g., a protease activity, a kinase activity, a phosphatase activity, a phosphodiesterase activity, a nucleotide cyclase activity, a ubiquitin ligase activity, a DNA polymerase activity, an RNA polymerase activity, a DNA ligase activity, and an isomerase activity.

Examples of types of proteases that can be detected, measured, or otherwise analyzed using a method or composition described herein include, but are not limited to: serine proteases (e.g., trypsin, chymotrypsin, elastase, or subtilisin), threonine proteases, cysteine proteases (e.g., papain, cathepsins, caspases, or calpains), asparatic acid proteases (e.g., HIV-1 protease, chymosin, renin, or plasmepsin), metalloproteases, and glutamic acid proteases.

Kinases are enzymes capable of modifying a substrate by adding one or more phosphate groups to it (a process termed "phosphorylation"). The activity of a large number of different types of kinases can be detected or measured using the compositions and methods described herein. For example, the activity of a tyrosine kinase, threonine/serine kinase, saccharide kinase, or lipid kinase can be detected or measured. Exemplary kinases include, e.g., the Akt kinase family, Aurora kinase family, PDK1, MAPKAP K2, Erk kinase family, CAMK kinase family, cyclin dependent kinases (e.g., CDK1, CDK2, CDK4, CDK6), RAF kinase family, casein kinase family, PKC family, PKA family, PKB family, PKG family, GSK3 beta, ROCK, SGK, Rsk family and Nek family; a protein tyrosine kinase including receptor tyrosine kinases, such as FGFR, EGFR, PDGFR, c-Kit, IGFR, insulin receptor, TrkA, TrkB, TrkC, c-Met or c-Ret, and cytoplasmic tyrosine kinases, such as Src, Lck, Lyn, Fyn, Yes, Syk, Hck, Abl and Eph family; or a lipid kinase, such as PI3 kinase, P14 kinase, or P15 kinase.

Phosphatases are capable of removing a phosphate moiety from a substrate. Phosphatase activity can include, e.g., tyrosine-specific phosphatase, threonine/serine phosphatase, dual-specificity phosphatase, saccharide phosphatase, histidine-specific phosphatase, or lipid phosphatase activity.

Phosphodiesterases (e.g., cyclic nucleotide phosphodiesterases) comprise a large group of enzymes organized into 11 distinct families based on biochemical and molecular properties. For example, PDEs include human Phosphodiesterase 3B, human Phosphodiesterase 11A1, human Phosphodiesterase 4A4, human Phosphodiesterase 4D3, and calf spleen Phosphodiesterase (Type II).

The enzymatic activity can be capable of modifying the target-selective binding agent and/or the target-selective binding agent. For example, the enzymatic activity can phosphorylate the target molecule or the target selective binding agent.

In some embodiments of the method, a decreased binding between the target molecule and the target-selective binding agent in the presence of a sample as compared to the amount of binding in the absence of the sample indicates the presence or amount of an enzymatic activity in the sample. For example, the presence of a particular protease activity in a sample that is capable of removing a portion of the target molecule that binds to the target-selective binding agent could be detected by way of a reduction in the amount of binding between the target molecule and the target-selective binding agent. In another example, where the target-selective binding agent preferentially binds to a non-phosphorylated target molecule and a phosphate moiety is removed by a particular phosphatase, the presence or amount of the phosphatase in a sample can be determined as a reduction in binding between a target-selective binding agent and a phosphorylated target molecule.

In some embodiments of the method, an increased binding between the target molecule and target-selective binding agent in the presence of a sample as compared to the amount of binding in the absence of the sample indicates the presence or amount of an enzymatic activity in the sample. For example, where a target-selective binding agent preferentially binds to a phosphorylated target molecule and the target molecule is phosphorylated by a particular kinase, the presence or amount of the kinase in a sample can be determined by an increase in the amount of binding between the target-selective binding agent and the target molecule.

Identifying a Compound that Modulates an Interaction or Enzymatic Activity

Also featured herein are methods for identifying a compound that modulates the binding between a target molecule and a target-selective binding agent. The methods can include the steps of: contacting, in the presence of a candidate compound, a first solid-phase support and a target molecule, wherein the first solid-phase support is associated with a target-selective binding agent and a first member of a Fluorescence Resonance Energy Transfer (FRET) pair and the target molecule is associated with a second member of the FRET pair, and wherein the target molecule is not associated with a second solid-phase support; and detecting binding of the target molecule to the target-selective binding agent, wherein a difference in binding of the target molecule to the target-selective binding agent in the presence of the candidate compound as compared to the binding in the absence of the candidate compound indicates that the candidate compound modulates the interaction between the target-selective binding agent and the target molecule.

The methods can also include the step of covalently or non-covalently binding the second member of the FRET pair to the target molecule and/or covalently or non-covalently binding the target-selective binding agent to the solid-phase support. Methods for covalent or non-covalent binding are described in detail above.

The methods can include the step of, after contacting the target-selective binding agent (associated with the solid-phase support) and the target molecule, separating the solid-phase support from the unbound target molecule (as described above).

A candidate compound can be contacted with a target molecule prior to contacting the target molecule with the target-selective binding agent. A candidate compound can be contacted with the target-selective binding agent prior to contacting the target-selective binding agent and the target molecule. In some embodiments, the target-selective binding agent can be contacted with the target molecule in the presence of the candidate compound (that is, the target molecule and target-selective binding agent are both contacted with the candidate compound at the same time).

The candidate compound can be, e.g., any of the compounds described herein (see below under "Compounds"). The candidate compound can be a compound that inhibits or enhances the binding between the target-selective binding agent and the target molecule.

In some embodiments of the methods, a decreased binding between the target molecule and the target-selective binding agent in the presence of a candidate compound as compared to the amount of binding in the absence of the compound indicates that the compound inhibits the interaction between the target-selective binding agent and the target molecule.

In some embodiments of the method, an increased binding between the target molecule and the target-selective binding agent in the presence of a candidate compound as compared to the amount of binding in the absence of the compound indicates that the compound enhances the interaction between the target-selective binding agent and the target molecule.

Methods for identifying a compound that modulates the activity of an enzyme can include the steps of providing: a first solid-phase support associated with a target-selective binding agent and a first member of a Fluorescence Resonance Energy Transfer (FRET) pair; a target molecule comprising a second member of the FRET pair, wherein the target molecule is not associated with a second solid-phase support; and an enzyme capable of modifying one or both of the target-selective binding agent and the target molecule; contacting, in the presence of the enzyme and a candidate compound, the first solid-phase support and the target molecule; and detecting binding of the target molecule to the target-selective binding agent, wherein a difference in binding of the target molecule to the target-selective binding agent in the presence of the candidate compound as compared to the binding in the absence of the candidate compound indicates that the candidate compound modulates the activity of the enzyme.

The methods can also include the step of covalently or non-covalently binding the second member of the FRET pair to the target molecule and/or covalently or non-covalently binding the target-selective binding agent to the solid-phase support. Methods for covalent or non-covalent binding are described above.

The methods can include the step of, after contacting the target-selective binding agent (associated with the solid-phase support) and the target molecule, separating the solid-phase support from the unbound target molecule (as described above).

An enzyme and candidate compound can be contacted with a target molecule prior to contacting the target molecule with the target-selective binding agent. An enzyme and candidate compound can be contacted with the target-selective binding agent prior to contacting the target-selective binding agent and the target molecule. In some embodiments, the target-selective binding agent can be contacted with the target molecule in the presence of the enzyme and the candidate compound.

The candidate compound can be, e.g., any of the compounds described herein (see below under "Compounds"). The candidate compound can be a compound that inhibits or enhances the binding between the target-selective binding agent and the target molecule.

The enzyme can be, e.g., any of those described herein.

In some embodiments of the methods, a decreased binding between the target molecule and the target-selective binding agent in the presence of a candidate compound as compared to the amount of binding in the absence of the compound indicates that the candidate compound inhibits the activity of the enzyme. In some embodiments of the method, an increased binding between the target molecule and the target-selective binding agent in the presence of a candidate compound as compared to the amount of binding in the absence of the compound indicates that the compound enhances the enhances the activity of the enzyme.

For example, where the target molecule is capable of being phosphorylated by a kinase and the target-selective binding agent is capable of binding to phosphorylated forms of the target molecule (e.g., deferoxamine and a trivalent metal cation), the activity of a kinase can be determined by the amount of binding between the target-molecule and target-selective binding agent in the presence of the kinase. As described above, the target molecule can be incubated with the kinase (under conditions that allow for the phosphorylation of the target molecule) in the presence and absence of a candidate compound. A decreased amount of binding of the target-selective binding agent to the target molecule in the presence of the candidate compound as compared to the binding of the target-selective binding agent to the target molecule in the absence of the compound indicates that the compound inhibits the activity of a kinase. Conversely, an increased amount of binding of the target-selective binding agent to the target molecule in the presence of the candidate compound as compared to the binding of the target-selective binding agent to the target molecule in the absence of the compound indicates that the compound enhances the activity of the kinase.

In some embodiments of the methods, a increased binding between the target molecule and the target-selective binding agent in the presence of a candidate compound as compared to the amount of binding in the absence of the compound indicates that the candidate compound inhibits the activity of the enzyme. In some embodiments of the method, decreased binding between the target molecule and the target-selective binding agent in the presence of a candidate compound as compared to the amount of binding in the absence of the compound indicates that the compound enhances the enhances the activity of the enzyme.

Multiplex Assay Formats

Also featured are multiplex assay methods to screen for, e.g.: (i) more than one compound that modulates an interaction between a target-molecule and a target-selective binding agent; (ii) more than one compound that can modulate the activity of an enzymatic activity; (iii) more than one enzymatic activity in a sample; or (iv) the specificity of an interaction between a target molecule and a target-selective binding agent. The multiplex methods can involve two or more (e.g., three, four, five, six, seven, eight, nine, 10, 12, 15, 20, 25, 30, 35, 40, 45, 50, 55, 60, 65, 70, 75, 80, 85, 90, 95, 96, 100, 200, 300, 386, 400, 500, or 1000 or more) sets of the same composition or two or more different sets of compositions.

For example, the multiplex assay methods can utilize, e.g., a first set of a first solid-phase support and a target molecule and a second set of the first solid-phase support and target molecule, wherein: (i) the first solid phase support is an assay particle; (ii) each solid-phase support is associated with a first member of a FRET pair and the same target-selective binding agent; and (iii) the target molecule is associated with a second member of the FRET pair. The first set can be placed into one well of a multi-well assay plate and the second set can be placed in another well of the multi-well assay plate. The two sets can then be contacted in parallel with different samples or different candidate compounds and the interaction between the target molecule and target-selective binding agent of each set evaluated individually. It is understood that each well of, e.g., a multi-well assay plate (e.g., 96 wells or 386 wells) can contain a set of the first solid-phase support and target molecule and thus, multiple different samples or candidate compounds can evaluated in parallel.

In another example, the multiplex assay methods can utilize a first set of a first solid-phase support and target molecule and a second set of the first solid-phase support and target molecule, wherein the first solid phase support is an assay particle and wherein each solid-phase support is associated with a different target-selective binding agent. In one instance, the first set can be placed into one well of a multi-well assay plate and the second set can be placed in another well of the multi-well assay plate. The binding between the target molecule and the different target-selective binding agents of the two sets can then be evaluated. For example, where the different target-selective binding agents are polynucleotide sequences and the target molecule (the same in both sets) is a nucleic-acid binding protein (NABP; such as a transcription factor), the specificity for each of the different polynucleotide sequences can be determined by the amount of binding in each set. If the binding of the NABP to the first polynucleotide sequence is greater than the binding of the NABP to the second polynucleotide sequence, this indicates that the NABP preferentially binds to the first polynucleotide sequence.

In another example, where one of the target-selective binding agents is a first recognition site variant for a kinase, the other target-selective binding agent is a second recognition site variant for the kinase, and the target molecule is capable of binding to phosphorylated forms of the variants (e.g., deferoxamine and a trivalent metal cation), the preference by the kinase for one recognition site variant over the other can be determined. For example, each of the sets can be contacted separately with a sample containing a known amount of the kinase for a time sufficient to allow phosphorylation of the recognition site variants. The binding between the first recognition site variant and the target molecule and the binding between the second recognition site variant and the target molecule is then compared. An increased amount of binding of the target molecule to the first recognition site variant as compared to the binding of the target molecule to the second recognition site variant is an indication that the kinase preferentially phosphorylates the first recognition site variant. Methods of designing/generating such recognition site variants are described in, e.g., Kim et al. (1999) J. Biol. Chem. 274(53):37538-37543 and Yang and Huang (1994) J. Biol. Chem. 269(47):29855-29859.

In yet another example, where one of the target-selective binding agents is a substrate for a first kinase, the other target-selective binding agent is a substrate for a second kinase, and the target molecule is capable of binding to phosphorylated forms of the substrates (e.g., deferoxamine and a trivalent metal cation), the presence of more than one kinase activity in a sample can be detected. The binding between the substrate for the first kinase and the target molecule and the binding between the second kinase substrate and the target molecule can be determined. An increased amount of binding in one or both of the wells contacted with the sample (as compared to amount of binding in the absence of the sample) indicates the presence of one or both of the kinases in the sample.

In another instance, the first set and second set of compositions containing different target-selective binding agents can be combined in a mixture. As noted above, in cases of mixtures of solid-phase support particles with different target-selective binding agents, the solid-phase support particles can be encoded such that each particle not only corresponds to a different target-selective binding agent, but that each different target-selective binding agent can be identified based on its unique particle code ID. In one example, where one of the target-selective binding agents is a substrate for a first kinase, the other target-selective binding agent is a substrate for a second kinase, and the target molecule is capable of binding to phosphorylated forms of the substrates (e.g., deferoxamine and a trivalent metal cation), the presence of more than one kinase activity in a sample can be detected. The binding between the substrate for the first kinase and the target molecule and the binding between the second kinase substrate and the target molecule can be determined. An increased amount of binding in one or both of the wells contacted with the sample (as compared to amount of binding in the absence of the sample) indicates the presence of one or both of the kinases in the sample.

Any of the methods for detection (or any screening methods described herein) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting FRET. Specific instruments that can be used in conjunction with the methods and compositions described herein include, e.g., the Victor™, EnVision™, Fusion™, and ViewLux™ apparatuses commercially available from PerkinElmer (Boston, Mass.).

Samples

A sample can be any composition. The content of the sample can be known or unknown. In many cases, a sample contains or is suspected of containing one or more enzymatic activities. A sample can be derived from an organism or can be a man-made source of enzyme. A sample can be, e.g., one containing one or more enzymes in a known quantity or with a known activity.

In some embodiments, a sample can contain one or more target molecules (e.g., any of the target molecules described herein) or one or more target molecules associated with a second member of a FRET pair.

A sample can be, for example, a specimen obtained from an individual or can be derived from such a specimen. For example, a sample can be a tissue section obtained by biopsy, or cells that are placed in or adapted to tissue culture. A sample can also be, or contain, a biological fluid specimen such as urine, blood, plasma, serum, saliva, semen, sputum, cerebral spinal fluid, tears, mucus, sweat, milk, semen, and the like. Biological samples can also be, or contain, fluid from ulcers or other surface eruptions such as blisters and abscesses or can be extracts of tissues from biopsies of normal, malignant, or suspect tissues. A sample can be further fractionated, if desired, to a fraction containing particular components or cell types. For example, a blood sample can be fractionated into serum or into fractions containing particular types of blood cells such as red blood cells or white blood cells (leukocytes). If desired, a sample can be a combination (pool) of samples from an individual such as a combination of a tissue and fluid sample, and the like.

A sample can be processed to facilitate detection of enzymes or their enzymatic acitivity. For example, if the sample includes cells or other biological structures, the sample can be treated with freeze/thaw treatment, drying and rehydrating, a dounce, detergent or other methods. Releasing or solubilizing enzymes can also be useful provided it does not interfere with the enzyme activity or the relevant assay method.

The sample can be obtained from body fluids and tissues in which particular enzymes being tested are typically expressed, e.g., liver enzymes obtained from liver.

Samples can be treated with customary care to preserve enzymatic activity and/or the activity or structure of target molecules and target-selective binding agents. For example, where a target molecule is isolated from a natural source such as a cell lysate, the cell lysate can be treated with a variety of buffering agents and/or inhibitors of proteolytic or nuclease activities that may affect the structure or function of the molecule. Suitable methods for obtaining samples that preserve the activity or integrity of enzymes, target molecules, or target-selective binding agents in the sample are well known to those skilled in the art. Such methods include the use of appropriate buffers and/or inhibitors, including nuclease, protease and phosphatase inhibitors that preserve or minimize changes in enzymes in the sample. Such inhibitors include, for example, chelators such as ethylenediamne tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Inhibitors can be chosen such that they do not interfere with or only minimally adversely affect the enzymatic activity of interest. For example, if the enzymatic activity to be detected is a protease, methods for obtaining samples that preserve the activity or integrity of the enzyme would not include protease inhibitors that adversely affect the particular protease activity. Appropriate buffers and conditions for enzyme-containing samples are well known (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)).

A sample can be processed to eliminate or minimize the presence of interfering substances, as appropriate. If desired, a sample can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like (Ausubel et al. supra, 1999; Scopes, Protein Purification: Principles and Practice, third edition, Springer-Verlag, New York (1993); Burton and Harding, J. Chromatogr. A 814:71-81 (1998)).

For use in a method described herein, a sample can be in a variety of physical states. For example, a sample can be a liquid or solid, can be dissolved or suspended in a liquid, can be in an emulsion or gel, and can be absorbed onto a material.

One or more properties of a sample can be modified, such that the sample allows or more effectively allows, a binding interaction to occur and/or an enzyme to act on a substrate. Such properties are well known to those skilled in the art and generally include salt concentration, pH, surfactant property, viscosity, and temperature.

Compounds

Candidate compounds that can be screened in any of the methods described herein include various chemical classes. Compounds can be biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs. Compounds can be both small or large molecule compounds.

Typically small molecule compounds are relatively small organic molecules having a molecular weight in the range of about 50 to 2,500 daltons. These compounds can comprise functional groups necessary for structural interaction with proteins (e.g., hydrogen bonding), and can include at least an amine, carbonyl, hydroxyl, or carboxyl group, and preferably at least two of the functional chemical groups. These compounds can often comprise cyclical carbon or heterocyclic structures and/or aromatic or polyaromatic structures (e.g., purine core) substituted with one or more of the above functional groups.

Also of interest as small molecule compounds in some of the methods described herein are nucleic acid aptamers, which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 8-16 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74:5-13, the disclosure of which is incorporated herein by reference in its entirety].

Large molecule compounds can include large proteins such as antibodies (see below) or macromolecular complexes comprising two or more proteins.

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods.

Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Bioechnol. 8:701-707 (1997).

Identification of compounds through the use of the various libraries described herein permits subsequent modification of the test compound "hit" or "lead" to optimize the capacity of the "hit" or "lead" to inhibit the interaction between, e.g., a target-selective binding agent and a target molecule.

Compounds can be large molecules such as antibodies, or antigen-binding antibody fragments, specific for, e.g., a target molecule or a target-selective binding agent. Such antibodies and fragments thereof will generally bind to, or close to: (a) the region of the target-selective binding agent to which the target molecule binds; or (b) the region of the target molecule to which the target-selective binding agent binds. However, the compounds can also act allosterically and so they can also bind to the target molecule or target-selective binding agent at positions other than the regions of the two molecules that mediate their interaction, but which otherwise affect their interaction. As used throughout the present application, the term "antibody" refers to a whole antibody (e.g., IgM, IgG, IgA, IgD, or IgE) molecule that is generated by any one of a variety of methods that are known in the art. The antibody can be made in, or derived from, any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, Current Protocols In Immunology, Coligan et al., ed. 2.8, 2.10 (Wiley Interscience, 1991), the disclosure of which is incorporated herein by reference in their entirety. scFv fragments can be produced, for example, as described in U.S. Pat. No. 4,642,334, the disclosure of which is incorporated herein by reference in its entirety.

The compounds identified above can be synthesized by any chemical or biological method or can be obtained from a natural source. The compounds identified above can also be pure, or can be in a formulation (e.g., a pharmaceutical composition) with one or more additional non-active ingredients (e.g., additional compounds or constituents which do not bind to or inhibit the interaction between a target-selective binding agent and a target molecule), and can be prepared in an assay-, physiologic-, or pharmaceutically-acceptable diluent or carrier.

Kits

The disclosure also features a variety of kits that can be used in connection with any of the methods described herein. The kits can include any of the compositions described herein. For example, the kits can contain a first solid-phase support associated with a target-selective binding agent and a first member of a Fluorescence Resonance Energy Transfer (FRET) pair; a target molecule comprising a second member of the FRET pair, wherein the target molecule is not associated with a second solid-phase support; and instructions for detecting the binding of a target molecule to a target-selective binding agent.

The disclosure also features kits comprising a first solid-phase support associated with a target-selective binding agent and a first member of a Fluorescence Resonance Energy Transfer (FRET) pair; a second member of the FRET pair; and instructions for covalently or non-covalently binding the second member of the FRET pair to a target molecule. The kits can also contain a target molecule and/or instructions for detecting the binding of a target molecule to a target-selective binding agent. The kits can also contain one or more reagents useful for isolating a target molecule from a natural source (e.g., a tissue or a cell) and/or one or more reagents for preparing a target molecule such as in vitro transcription/translation reagents.

The kits can also contain, e.g., a control compound that inhibits the interaction between the target molecule and the target-selective binding agent and/or a control compound that enhances the interaction between the target molecule and the target-selective binding agent.

The kits can include an assay vessel such as a microcentrifuge tube or a multi-well assay plate. In addition, the kits can include one or more reagents for performing an enzymatic reaction (e.g., a kinase reaction, a phosphatase reaction, a protease reaction, a phosphodiesterase reaction, or any of the enzymatic reactions described herein). The one or more reagents can include, e.g., a nucleotide triphosphate, a magnesium salt (e.g., $MgCl_2$), and/or a manganese salt ($MnCl_2$).

The kits can also contain a control sample. The control sample can be any of those described herein and can contain, e.g., one or more (e.g., two, three, four, five, or six) enzymes at a known concentration. The kits can also contain any number of aqueous buffers for evaluating the binding between a target molecule and a target selective binding agent. The kits can contain buffers for use in washing steps of binding assays.

The kits can contain one or more solutions that enhance FRET between the first and second member of the FRET pair.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A composition comprising:
   a first solid-phase support comprising a target-selective binding agent and a first member of a Fluorescence Resonance Energy Transfer (FRET) pair; and
   a target molecule associated with a second member of the FRET pair, wherein the target molecule is not associated with a solid-phase support;
   wherein the first solid-phase support comprises phthalocyanine and thioxene;
   wherein the first member of the FRET pair is a lanthanide chelate; and
   wherein the target-selective binding agent comprises deferoxamine-$Fe^{3+}$ and preferentially binds to a target molecule that comprises a phosphomonoester moiety as compared to a target molecule that does not comprise a phosphomonoester moiety.

2. The composition of claim 1, wherein the first solid-phase support is an assay plate.

3. The composition of claim 1, wherein the first solid-phase support is a particle.

4. The composition of claim 1, wherein the lanthanide chelate comprises a lanthanide selected from the group consisting of europium, terbium, samarium, and dysprosium.

5. The composition of claim 1, wherein the composition comprises at least two first solid-phase supports, each first solid-phase support comprising a different target-selective binding agent.

6. The composition of claim 1, wherein the first solid-phase support is a particle having a diameter between about 100 nm and 1000 nm.

7. The composition of claim 1, wherein the first solid-phase support is a particle having a diameter between about 100 nm and 400 nm.

8. The composition of claim 1, wherein the composition is in suspension or is lyophilized.

9. The composition of claim 1, wherein the composition further comprises an aqueous buffer in which the composition forms a suspension or solution.

10. The composition of claim 1, wherein the target molecule comprises one or more of a polypeptide, a nucleic acid, a carbohydrate, and a small molecule.

11. The composition of claim 10, wherein the target molecule comprises a polypeptide.

12. The composition of claim 10, wherein the target molecule comprises a nucleic acid.

13. The composition of claim 10, wherein the target molecule comprises a carbohydrate.

14. The composition of claim 10, wherein the target molecule comprises a small molecule.

* * * * *